(12) United States Patent
Tanaka et al.

(10) Patent No.: US 8,419,841 B2
(45) Date of Patent: Apr. 16, 2013

(54) AIR PROCESSING DEVICE

(75) Inventors: Toshio Tanaka, Osaka (JP); Kanji Motegi, Osaka (JP); Tsunahiro Ohdou, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 345 days.

(21) Appl. No.: 12/920,590

(22) PCT Filed: Mar. 3, 2009

(86) PCT No.: PCT/JP2009/000957
§ 371 (c)(1),
(2), (4) Date: Sep. 2, 2010

(87) PCT Pub. No.: WO2009/113269

PCT Pub. Date: Sep. 17, 2009

(65) Prior Publication Data

US 2011/0000374 A1  Jan. 6, 2011

(30) Foreign Application Priority Data

Mar. 11, 2008  (JP) ................. 2008-061592

(51) Int. Cl.
*B03C 3/70* (2006.01)
(52) U.S. Cl.
USPC ............... 96/83; 96/88; 174/110 R; 174/154
(58) Field of Classification Search .............. 96/52, 53, 96/83, 88; 174/110 R, 154, 167, 168
See application file for complete search history.

(56) References Cited

U.S. PATENT DOCUMENTS

| | | | | |
|---|---|---|---|---|
| 1,994,259 A | * | 3/1935 | Thorne | 174/31 R |
| 2,806,896 A | * | 9/1957 | Streuber et al. | 174/18 |
| 3,362,134 A | * | 1/1968 | Wiemer | 96/26 |
| 4,177,047 A | * | 12/1979 | Goland | 96/88 |
| 4,251,682 A | * | 2/1981 | Ebert et al. | 95/57 |
| 4,294,591 A | * | 10/1981 | Kahl | 96/43 |
| 5,006,134 A | * | 4/1991 | Knoll et al. | 96/88 |
| 5,421,863 A | * | 6/1995 | Rector et al. | 96/60 |
| 5,584,915 A | * | 12/1996 | Broughton | 96/32 |
| 6,663,696 B1 | * | 12/2003 | Miller et al. | 96/88 |
| 7,261,764 B1 | * | 8/2007 | Pletcher | 95/58 |
| 2004/0226449 A1 | * | 11/2004 | Heckel et al. | 96/88 |

FOREIGN PATENT DOCUMENTS

| | | | | |
|---|---|---|---|---|
| JP | 32-8888 Y1 | 8/1957 | | |
| JP | 39-30752 Y1 | 10/1964 | | |
| JP | 51-3097 Y2 | 1/1976 | | |
| JP | 52-60476 A | * | 5/1977 | 96/88 |
| JP | 59-131250 U | 9/1984 | | |
| JP | 1-258754 A | * | 10/1989 | 96/88 |

(Continued)

*Primary Examiner* — Richard L Chiesa
(74) *Attorney, Agent, or Firm* — Birch, Stewart, Kolasch & Birch, LLP

(57) ABSTRACT

An air processing device is provided by which a current-carrying section is attached to a casing by an insulating member having a covering section covering an outer periphery face of a current-carrying section and a tube-like section in which a power source-side end of the covering section is supported by a tube bottom section. This consequently secures a long insulating distance from an electric discharge spray section and a charged dust collecting section via the current-carrying section to the casing. As a result, the respective electrodes and the casing can have an improved insulating performance therebetween even under an environment where water droplets are supplied.

6 Claims, 4 Drawing Sheets

FOREIGN PATENT DOCUMENTS

| | | |
|---|---|---|
| JP | 6-31203 A | 2/1994 |
| JP | 6-246187 A | 9/1994 |
| JP | 10-235227 A | 9/1998 |
| JP | 2002-204823 A | 7/2002 |
| JP | 2002-260466 A | 9/2002 |
| JP | 2005-74330 A | 3/2005 |
| JP | 2007-29845 A | 2/2007 |

* cited by examiner

AIR PROCESSING DEVICE

This application is a National Phase of International Application No. PCT/JP2009/000957 filed Mar. 3, 2009, and claims priority under 35 U.S.C. §119 to Japanese Application No. 2008-061592 filed Mar. 11, 2008, the entire contents of which are hereby incorporated by reference.

TECHNICAL FIELD

The present invention relates to an air processing device.

BACKGROUND ART

Conventionally, air processing devices for removing dust or odor substances, etc. in air have been known. Such air processing devices have been widely used for applications such as the cleaning of a room interior or the processing of exhaust gas from a kitchen or a plant for example.

Patent Document 1 discloses an air processing device that processes exhaust gas discharged from a kitchen. This air processing device includes a charged dust collecting section that is provided in an air passageway through which air flows. The charged dust collecting section has a charging section and a dust collecting section. In the charging section, corona discharge is generated. By this corona discharge, dust in air (including oily smoke and steam for example) is charged to have a predetermined charge. The dust collecting section includes a dust collecting electrode. The charged dust is electrically-induced to the dust collecting electrode. As a result, the dust in air is captured at a surface of the dust collecting electrode.

By the way, in the case of the air processing device including the charged dust collecting section as described above, the dust adhered to the respective electrodes of the charging section and the dust collecting section undesirably causes a gradual deterioration of the dust collecting performance. In the case of the air processing device as disclosed in Patent Document 1 for processing the exhaust gas from a kitchen in particular, air to be processed includes a large amount of oil mist. Thus, an oil film tends to be formed on a surface of the dust collecting electrode for example and thus the dust collecting performance tends to deteriorate.

To prevent this, an approach may be considered where a spray section for spraying water to air is provided and, in the charged dust collecting section, dust adhered to a surface of a dust collecting-side electrode for example is washed away by the sprayed water from the spray section to thereby secure an effective surface area used for dust collection, thereby suppressing the dust collecting performance from deteriorating.

CITATION LIST

Patent Document 1: Japanese Laid-Open Publication No. 2007-29845

SUMMARY OF THE INVENTION

Technical Problem

In the conventional air processing device however, water droplets are supplied to the interior of a casing in order to wash away dust. This causes a risk where, even when the casing is insulated from the respective electrodes such as the charging section and the dust collecting section, water droplets may adhere to the respective electrodes to thereby cause current leakage from a side wall of the casing via a current-carrying section for applying a voltage to the respective electrodes.

The present invention has been made in view of the point as described above. It is an objective of the invention to provide an air processing device by which the casing and the respective electrodes can have an improved insulating performance therebetween even under an environment where water droplets are supplied.

Solution to the Problem

In order to achieve the above-described objective, according to the present invention, a current-carrying section for electrically connecting a power source to an electric discharge processing section is attached to a casing via an insulating member having an insulation property.

Specifically, the present invention is for an air processing device including an electric discharge processing section (20, 30) that is provided in an air passageway (15) in a casing (11) supplied with water droplets and to which a voltage is applied to perform electric discharge. The invention provides solution means as shown below.

More specifically, the first aspect of the invention includes a current-carrying section (45) that electrically connects a power source (23, 34) exterior to the casing (11) to the electric discharge processing section (20, 30) to apply a voltage to the electric discharge processing section (20, 30) and that is attached to the casing (11) via an insulating member (40) having an insulation property, wherein:

the insulating member (40) includes:

a covering section (46) covering an outer periphery face of the current-carrying section (45), and a tube-like section (41) that is formed to have a tube-like shape having a bottom, that is attached to the casing (11) so that an opening-side end is positioned in the air passageway (15), and that is structured so that a power source-side end of the covering section (46) is supported by a tube bottom section (41a) so that the current-carrying section (45) extends through the tube in a tube axis direction.

According to the second aspect of the invention, in the first invention, at a predetermined position in the covering section (46) at a tube inner side with respect to an opening-side end of the tube-like section (41), a flange section (46a) is provided that suppresses water from moving to the tube inner side along an outer periphery face of the covering section (46).

According to the third aspect of the invention, in the first or second aspect of the invention, the tube-like section (41) of the insulating member (40) is attached to the casing (11) so that an opening-side end is downwardly inclined.

According to the fourth aspect of the invention, in the first or second aspect of the invention, the current-carrying section (45) is horizontally attached to the casing (11) via the insulating member (40), and a drainage channel (42) that extends in a tube axis direction and that is downwardly inclined to an opening-side end is formed at the lowest part at an inner periphery face of the tube-like section (41).

According to the fifth aspect of the invention, in any one of the first to fourth aspects of the invention, at a predetermined position in an inner periphery face of the tube-like section (41) in a tube axis direction, a protrusion section (43) is provided that protrudes in a tube inner diameter direction and that suppresses water from moving along an inner periphery face of the tube-like section (41) to a tube inner side.

According to the sixth aspect of the invention, in any one of the first to fifth aspects of the invention, an air hole (44) for introducing air from the outside of the casing (11) into the air passageway (15) is formed at the tube bottom section (41a) of the tube-like section (41).

Advantages of the Invention

According to the first aspect of the invention, the current-carrying section (45) for electrically connecting the power source (23, 34) to the electric discharge processing section (20, 30) is attached to the casing (11) via the insulating member (40). This insulating member (40) is composed of the covering section (46) and the tube-like section (41). Thus, the electric discharge processing section (20, 30) and the casing (11) can have a sufficiently-secured insulating performance therebetween even when water droplets adhered to the insulating member (40) cause current flowing via the water droplets over the surface of the insulating member (40).

Specifically, current flowing via water droplets over the surface of the insulating member (40) firstly flows from the electric discharge processing section (20, 30) via the surface of the covering section (46) to the tube bottom section (41a) of the tube-like section (41). Then, current flows over the tube inner periphery face of the tube-like section (41) to the opening-side and then flows over the tube outer periphery face and reaches the casing (11). This can consequently secure a long insulating distance from the electric discharge processing section (20, 30) via the current-carrying section (45) to the casing (11). Thus, the electric discharge processing section (20, 30) and the casing (11) can have an improved insulating performance therebetween.

According to the second aspect of the invention, at a predetermined position in the covering section (46) at a tube inner side than an opening-side end of the tube-like section (41), the flange section (46a) is provided. This consequently suppresses water droplets having entered the tube interior from the opening-side of the tube-like section (41) via the surface of the covering section (46) from flowing to the tube inner side than the flange section (46a), thus blocking a current-carrying path. Thus, the electric discharge processing section (20, 30) and the casing (11) can have an improved insulating performance therebetween.

According to the third aspect of the invention, the tube-like section (41) of the insulating member (40) is attached to the casing (11) so that an opening-side end is downwardly inclined. Thus, water droplets having entered the tube interior from the opening are drained also from the opening-side along the inner periphery face. Thus, water droplets can be prevented from being accumulated in the tube interior, thus securing the insulating performance.

According to the fourth aspect of the invention, the drainage channel (42) that extends in a tube axis direction and that is downwardly inclined to an opening-side end is formed at the lowest part at an inner periphery face of the tube-like section (41). Thus, water droplets having entered the tube interior from the opening-side are drained via the drainage channel (42) again from the opening-side. Thus, water droplets can be prevented from being accumulated in the tube interior, thus securing the insulating performance.

According to the fifth aspect of the invention, at a predetermined position in an inner periphery face of the tube-like section (41) in a tube axis direction, a protrusion section (43) is provided that protrudes in a tube inner diameter direction.

Thus, water droplets having entered the tube interior from the opening-side of the tube-like section (41) along the inner periphery face are suppressed from flowing to the tube inner side than the protrusion section (43), thus blocking a current-carrying path. Thus, the electric discharge processing section (20, 30) and the casing (11) can have an improved insulating performance therebetween.

According to the sixth aspect of the invention, the tube bottom section (41a) of the tube-like section (41) includes the air hole (44). By the existence of the air hole (44), water droplets moving from the opening-side of the tube-like section (41) to the tube interior are pushed back to the opening-side by the air introduced through the air hole (44), thus blocking a current-carrying path. Thus, the electric discharge processing section (20, 30) and the casing (11) can have an improved insulating performance therebetween.

DESCRIPTION OF REFERENCE CHARACTERS

Figure 1:
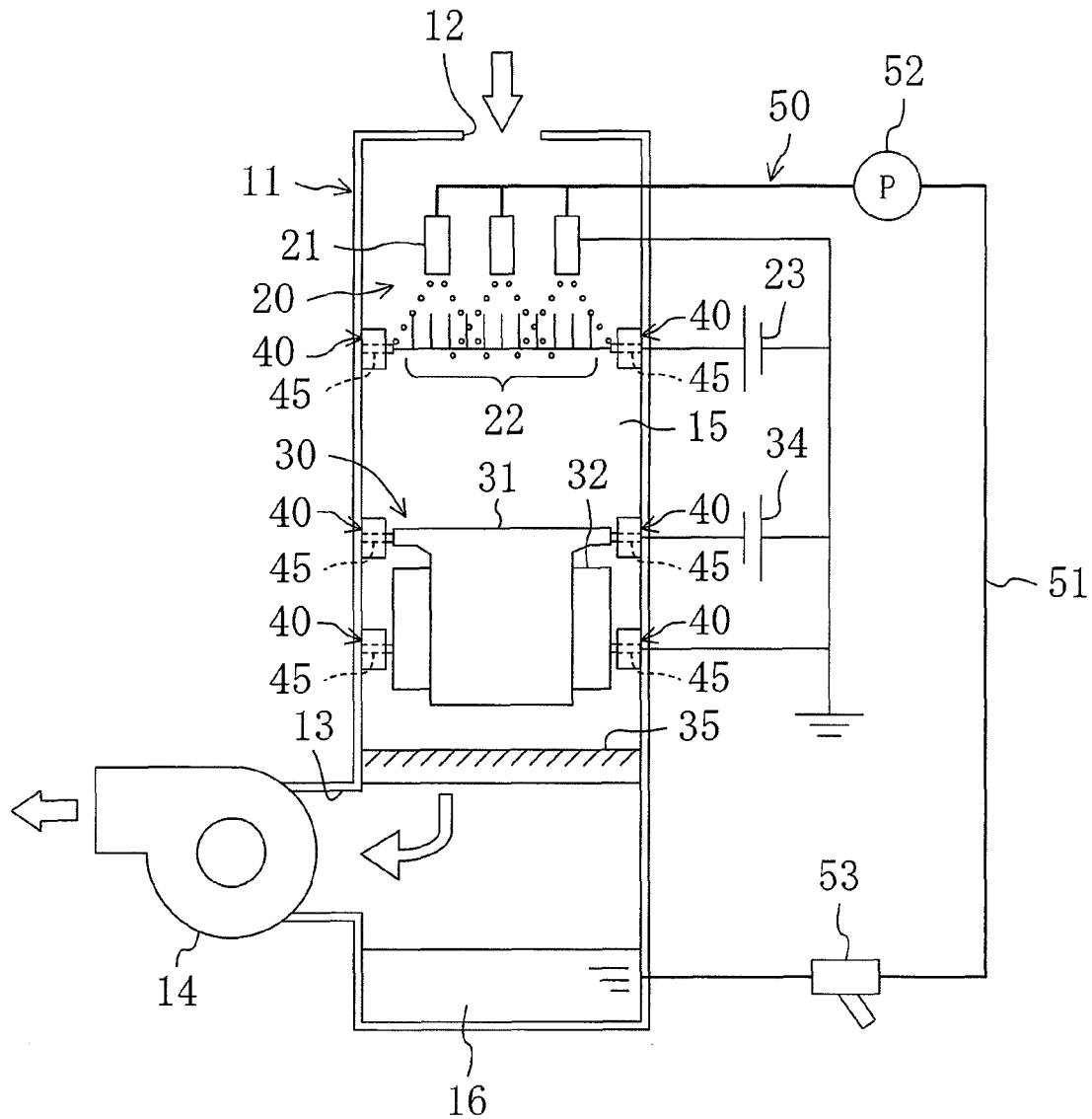
FIG. 1 is a cross-sectional view schematically illustrating the inner structure of an air processing device according to an embodiment of the present invention.

10 Air processing device
11 Casing
15 Air passageway
20 Electric discharge spray section (electric discharge processing section)
23 Power source
30 Charged dust collecting section (electric discharge processing section)
34 Power source
40 Insulating member
41 Tube-like section
41a Tube bottom section
42 Drainage channel
43 Protrusion section
44 Air hole
45 Current-carrying section
46 Covering section
46a Flange section

DESCRIPTION OF EMBODIMENTS

The following section will describe an embodiment of the present invention with reference to the drawings. The following description of a preferred embodiment is essentially a mere illustration and does not intend to limit the present invention or the use or application thereof.

FIG. 1 is a cross-sectional view schematically illustrating the inner structure of an air processing device (10) according to an embodiment of the present invention. As shown in FIG. 1, this air processing device (10) is used to process air discharged from a kitchen space of a restaurant or hotel for example (exhaust gas). The air processing device (10) removes oil mist (oil in the form of minute particles) in air, other harmful substances, and odor substances for example.

The air processing device (10) includes a vertically-long casing (11). The casing (11) is formed to have a hollow cylindrical or rectangular tube-like shape. At an upper part of the casing (11), a suction port (12) is opened. The suction port (12) is connected to the kitchen space via a duct (not shown) for example. At a side face for example of a lower part of the casing (11), a blowoff port (13) is opened. The blowoff port (13) faces an outdoor space. The blowoff port (13) includes a blast fan (14) for carrying air.

The casing (11) includes therein an air passageway (15) though which air flows from the suction port (12) to the blowoff port (13). More specifically, the casing (11) includes therein the air passageway (15) so that air flows downwardly. The casing (11) also includes, at the bottom section thereof, a storage tank (16). In the storage tank (16), sprayed water from a spray nozzle (21) (which will be described later) is collected and stored.

The air passageway (15) includes, in an order from the upper side to the lower side (from an upstream side to a downstream side of airflow), an electric discharge spray section (20) as an electric discharge processing section, a charged dust collecting section (30), and a demister section (35).

The electric discharge spray section (20) includes a plurality of spray nozzles (21) and electric discharge electrodes (22). The spray nozzle (21) is used to spray water to air and includes a spray opening facing downward. The spray nozzle (21) is configured so that sprayed water therefrom forms a hollow conical shape. In other words, in the vicinity of the spray nozzle (21), sprayed water exists only in an outer edge of the hollow conical region and does not substantially exist in the interior thereof.

An upper end of the spray nozzle (21) is connected to an outflow end of a water circulation flow path (51). An inflow end of the water circulation flow path (51) is connected to the storage tank (16). In other words, the water circulation flow path (51) constitutes a flow path for sending water collected in the storage tank (16) to the spray nozzle (21). The water circulation flow path (51) includes, in an order from the outflow side to the inflow side, a water circulation pump (52) and a water filter (53).

The water circulation pump (52) constitutes a water carrying means for pumping the water collected in the storage tank (16) to the spray nozzle (21). A water filter (53) is a means for physically capturing minute dust (solid particles) included in water flowing in the water circulation flow path (51) and constitutes a water clarification means for clarifying this water. The water circulation flow path (51) and the water circulation pump (52) constitute a water circulation mechanism (50) for sending the water collected in the storage tank (16) to the spray nozzle (21).

The spray nozzle (21) includes, at the lower side thereof, a plurality of electric discharge electrodes (22). Each of the electric discharge electrodes (22) is formed to have a needle-like or bar-like shape and is perpendicularly retained by the casing (11) for example. The electric discharge electrodes (22) have tip ends facing the spray openings of the spray nozzles (21). The respective electric discharge electrodes (22) are positioned in the hollow conical-shaped regions within which the sprayed water from the spray nozzles (21) exist.

The spray nozzle (21) and the electric discharge electrode (22) are connected to a power source (23) via a current-carrying section (45). The power source (23) is preferably a high-voltage DC power source but also may be an AC power source or a pulse power source. The power source (23) is preferably subjected to a so-called constant current control for providing a fixed current value of the electric discharge from the electric discharge electrode (22).

In this embodiment, the spray nozzle (21) is at a negative electrode-side and the electric discharge electrode (22) is at a positive electrode-side. A potential difference is applied from the power source (23) to the spray nozzle (21) and the electric discharge electrode (22). As a result, in the electric discharge spray section (20), a streamer discharge is generated from the electric discharge electrode (22) to the sprayed water.

Figure 2:
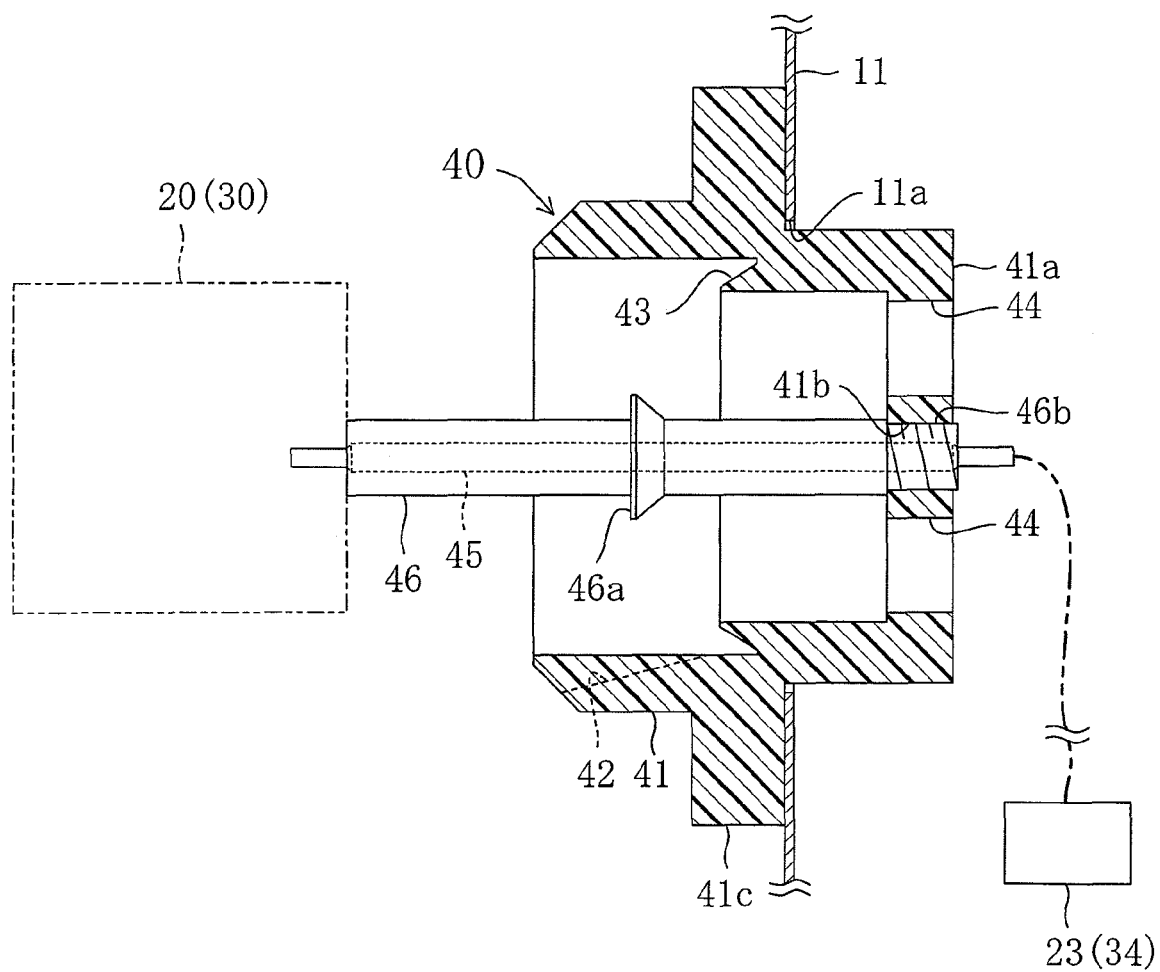
FIG. 2 is a side cross-sectional view illustrating the configurations of a current-carrying section and an insulating member.

FIG. 2 is a side cross-sectional view illustrating the configurations of a current-carrying section and an insulating member. As shown in FIG. 2, the current-carrying section (45) constitutes a current-carrying path for applying a voltage to the electric discharge electrode (22) and is horizontally attached to the casing (11) via an insulating member (40) having an insulation property.

The insulating member (40) includes: a covering section (46) covering the outer periphery face of the current-carrying section (45); and a tube-like section (41) that is formed to have a tube-like shape having a bottom, that is attached to the casing (11) so that an opening-side end is positioned in the air passageway (15), and that is structured so that the power source-side end of the covering section (46) is supported by the tube bottom section (41a) so that the current-carrying section (45) extends through the tube in the tube axis direction. Specifically, the power source-side end of the covering section (46) has a screw section (46b) that is screwed with a screw hole (41b) provided at substantially the center of the tube bottom section (41a) to thereby support the covering section (46) by the tube-like section (41).

Both ends of the current-carrying section (45) protrude from both ends of the covering section (46). By connecting the respective protruded parts to the electric discharge electrode (22)-side wiring and the power source (23)-side wiring, respectively, a voltage is applied from the power source (23) to the electric discharge electrode (22).

At a predetermined position in the covering section (46) at a tube inner side than an opening-side end of the tube-like section (41), a flange section (46a) is provided that suppresses water from moving to the tube inner side along an outer periphery face of the covering section (46). This suppresses water droplets having entered from the opening-side of the tube-like section (41) via the surface of the covering section (46) to the interior of the tube from flowing to the tube inner side than the flange section (46a) to thereby block a current-carrying path. Thus, the electric discharge electrode (22) and the casing (11) can have an improved insulating performance therebetween.

The outer periphery face of the tube-like section (41) has an attachment flange (41c) provided at substantially the center in the tube axis direction. At a side wall of the casing (11), an attachment hole (11a) is formed that is engaged with the tube-like section (41). A tube bottom section (41a) of the tube-like section (41) is inserted through the casing (11) to the attachment hole (11a). While the attachment flange (41c) is being abutted to an inner wall face of the casing (11), a fastening bolt (not shown) for example is used to fix the tube-like section (41) to thereby attach the tube-like section (41) to a side wall face of the casing (11).

The tube-like section (41) has, at the lowest part of the inner periphery face thereof, a drainage channel (42) that extends in the tube axis direction and that is downwardly inclined to the opening-side end. This allows water droplets having entered from the opening-side to the tube interior to be drained again from the opening-side via the drainage channel (42). Thus, water droplets can be prevented from being accumulated in the tube interior.

Figure 4:
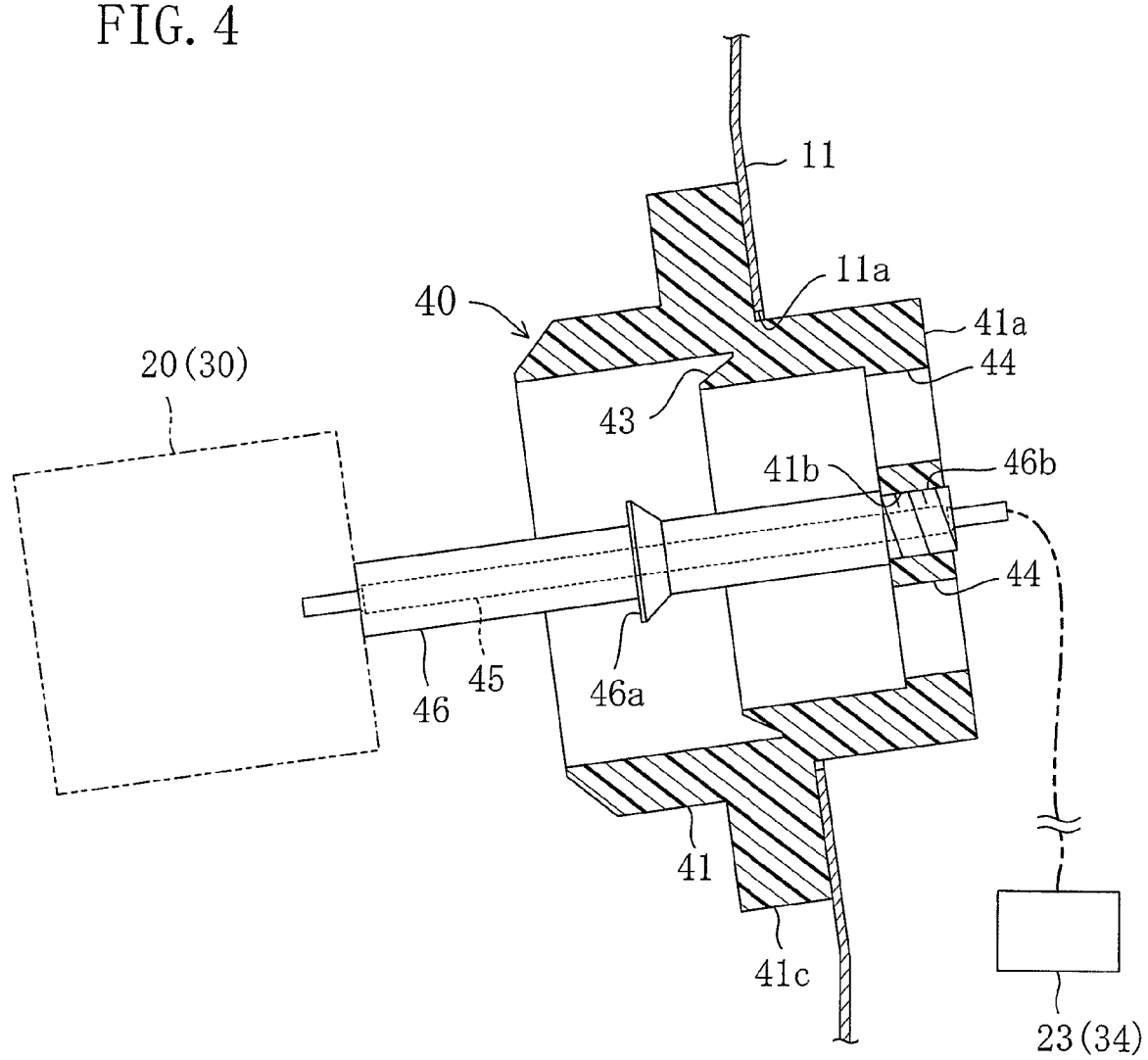
FIG. 4 is a side cross-sectional view illustrating a modification example of FIG. 2.

The invention is not limited to the configuration where the inner periphery face of the tube-like section (41) has the drainage channel (42). Other configurations as in FIG. 4 showing a modification example for example also may be used where the drainage channel (42) is not provided and the tube-like section (41) is attached to the side wall face of the casing (11) so that the opening-side end thereof is downwardly inclined. This configuration allows water droplets having entered from the opening-side to the tube interior to be drained again from the opening-side along the inner periphery face. Thus, water droplets can be prevented from being accumulated in the tube interior, thus securing the insulating performance.

At a predetermined position in the inner periphery face of the tube-like section (41) in the tube axis direction, a protrusion section (43) is provided that protrudes in the tube inner diameter direction and that suppresses the water from moving to the tube inner side along the inner periphery face of the tube-like section (41). This protrusion section (43) has a tapered tip end by which water droplets having entered from the opening-side of the tube-like section (41) along the inner periphery face to the tube interior are allowed to move along the tapered tip end. Thus, the water droplets are prevented from flowing into the tube inner side beyond the protrusion section (43), thus blocking a current-carrying path.

The tube bottom section (41a) of the tube-like section (41) includes an air hole (44) for introducing air from the outside of the casing (11) into the air passageway (15). By the existence of the air hole (44), water droplets moving from the opening-side of the tube-like section (41) to the tube interior are pushed back to the opening-side by the air introduced through the air hole (44). Thus, water is suppressed from adhering to the inner periphery face of the tube-like section (41).

By the configuration as described above, the electric discharge spray section (20) and the casing (11) can have a sufficient insulating performance therebetween even when water droplets adhered to an insulating member (40) cause current to flow via the water droplets over the surface of the insulating member (40).

Specifically, current flowing via water droplets over the surface of the insulating member (40) firstly flows from the electric discharge spray section (20) to the covering section (46) and reaches the tube bottom section (41a) of the tube-like section (41). Then, current flows over the tube inner periphery face of the tube-like section (41) toward the opening-side and subsequently flows over the tube outer periphery face and reaches the casing (11). Thus, a long insulating distance can be secured from the electric discharge spray section (20) via the current-carrying section (45) to the casing (11), thus allowing the electric discharge spray section (20) and the casing (11) to have an improved insulating performance therebetween.

Figure 3:
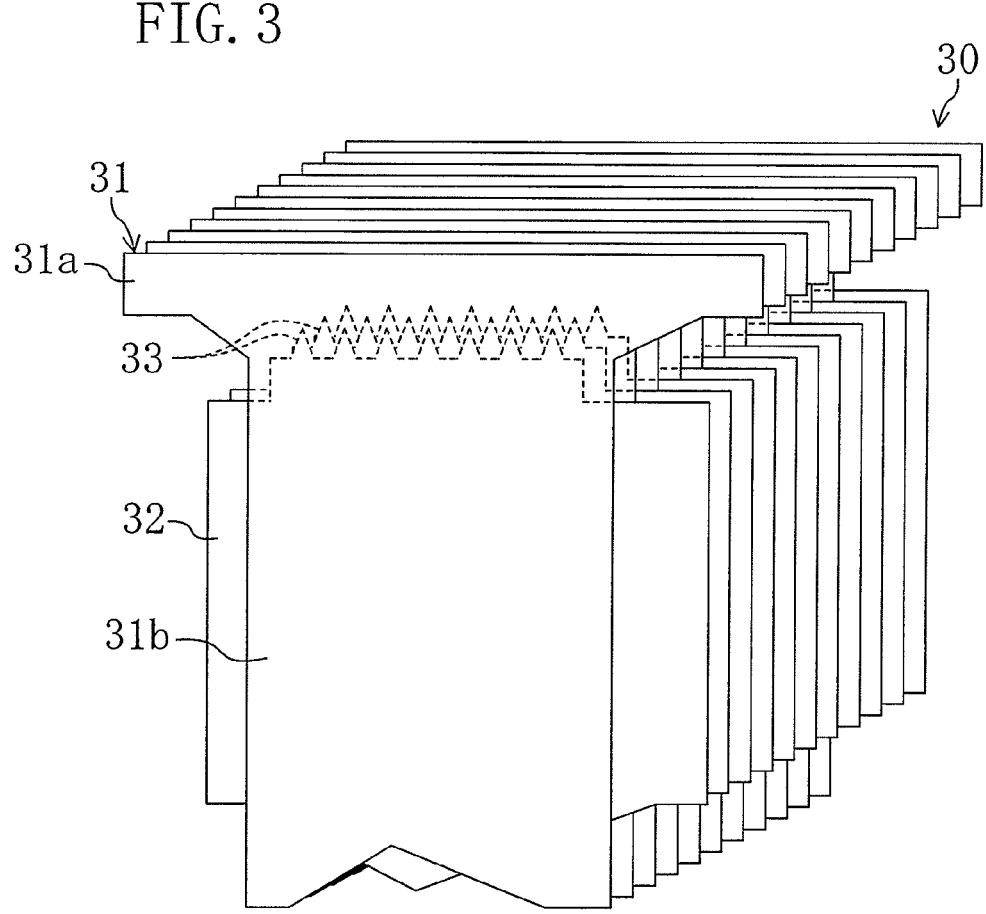
FIG. 3 is an expanded perspective view schematically illustrating a charged dust collecting section.

As shown in FIG. 1 and FIG. 3, the charged dust collecting section (30) includes the first electrode plates (31), the second electrode plates (32), and ionization electrodes (33).

The first electrode plate (31) is shaped like an elongayed plate. The air passageway (15) includes a plurality of first electrode plates (31) that are arranged to have a predetermined interval thereamong while being perpendicularly retained. The first electrode plate (31) is structured so that a substantial half of the upper side (upstream side) constitutes a charged electrode section (31a) and a substantial half of the lower side (downstream side) constitutes a dust collecting electrode section (31b). In other words, the first electrode plate (31) is composed of the charged electrode section (31a) and the dust collecting electrode section (31b) that are integratedly formed.

Each of the ionization electrodes (33) is provided at an intermediate position between neighboring charged electrode sections (31a). The ionization electrode (33) is obtained by forming a tip end of the second electrode plate (32) to have a saw-like shape. The ionization electrode (33) constitutes a sharp protrusion that upwardly protrudes to be parallel to the first electrode plate (31). The charged electrode section (31a) and the ionization electrode (33) constitute a charging section for electrostatically charging dust in air (mainly oil mist). The ionization electrode (33) may be separately formed from the second electrode plate (32) for example or also may be configured by a bar-like or linear ionization line for example.

Each of the second electrode plates (32) is provided at an intermediate position between neighboring dust collecting electrode sections (31b). The second electrode plate (32) is shaped as a plate that is parallel to the first electrode plate (31) and that extends horizontally. The second electrode plates (32) are arranged so as to face the respective neighboring dust collecting electrode sections (31b). The second electrode plate (32) and the dust collecting electrode section (31b) constitute a dust collecting section for electrically capturing dust electrostatically-charged by the charging section. The first electrode plates (31) and the second electrode plates (32) are connected to a power source (34) via the current-carrying section (45). In this embodiment, the first electrode plate (31) is at the positive electrode-side and the second electrode plate (32) is at the negative electrode-side.

Regarding the configurations of the current-carrying section (45) and the insulating member (40) for attaching the current-carrying section (45) to the casing (11), these configurations are the same as those described for the electric discharge spray section (20) and thus will not be further described below.

The demister section (35) constitutes a water droplet collecting means for physically capturing water droplets included in air.

—Operation—

Next, the following section will describe the operation of the air processing device (10) according to this embodiment. During the operation of the air processing device (10), the blast fan (14) and the water circulation pump (52) are in an operating status. At the same time, a voltage is applied from the power source (23) via the current-carrying section (45) to the spray nozzles (21) and the electric discharge electrodes (22) and a voltage is applied from the power source (34) to the first electrode plates (31) and the second electrode plates (32).

In accordance with the start of the blast fan (14), air discharged from a kitchen space is sucked through the suction port (12) into the casing (11). Air flowing in the air passageway (15) in the casing (11) flows downward and passes through the electric discharge spray section (20). In the electric discharge spray section (20), water sprayed from the spray nozzles (21) is subjected to a streamer discharge from the electric discharge electrodes (22).

By the streamer discharge as described above, in the electric discharge spray section (20), active species (e.g., high-speed electrons, ions, ozone, radicals, and other excited molecules (e.g., excited oxygen molecules, excited nitrogen molecules, excited water molecules)) are generated. Since an electric discharge field in particular is supplied with a large amount of water, the generation of OH radicals is promoted under the existence of water. Furthermore, the generated active species scatter together with sprayed water, thus improving the diffusion of active species.

Then, harmful substances and odor substance included in air react with the active species to cause oxidation decomposition therein and are subsequently removed. Hydrophilic substance in the odor substance is absorbed by sprayed water and is captured. Hydrophobic substance in the odor substance is oxidized by the active species and tends to turn to hydrophilic substance. Thus, the resultant hydrophilic odor substance is also absorbed by sprayed water and is captured.

As described above, in the electric discharge spray section (20), harmful substance for example is effectively removed by an oxidation decomposition action to harmful substance for example by a streamer discharge and an absorption/dissolution action (more specifically, scrubber action) to harmful substance for example using sprayed water from the spray nozzle (21). The removal of harmful substance for example as described above is similarly carried out at the downstream-side of the electric discharge spray section (20) in the air passageway (15).

Air having flowed out of the electric discharge spray section (20) further flows downwardly and passes through the charged dust collecting section (30). In the charged dust collecting section (30), air firstly passes between the charged electrode section (31a) and the ionization electrode (33). During this, a corona discharge is carried out between the ionization electrode (33) and the charged electrode section (31a). By this corona discharge, oil mist in air for example is negatively electrostatically charged. Thereafter, air passes between the second electrode plate (32) and the dust collecting electrode section (31b). As a result, the negatively electrostatically charged oil mist for example adheres to the surface of the dust collecting electrode section (31b) which is the positive side electrode. Specifically, in the dust collecting electrode section (31b), the oil mist for example is induced to a horizontally-provided dust collecting face and is captured. As a result, the oil mist in air for example is removed.

Air having flowed out of the charged dust collecting section (30) further flows downwardly and passes through the demister section (35). In the demister section (35), water droplets included in air is physically captured. In the manner as described above, air from which harmful substance, odor substance, oil mist, and water for example are removed is discharged through the blowoff port (13) to the outside of the room.

Water captured by the demister section (35) on the other hand drips down and is collected in the storage tank (16). The water collected in the storage tank (16) is sucked by the water circulation pump (52) into the water circulation flow path (51) and passes through the water filter (53) and is then again sprayed through the spray nozzle (21) into air.

Although the air processing device (10) of this embodiment is used to process exhaust gas from a kitchen space, this air processing device (10) also can be used as an air cleaner for general home use.

—Cleaning Action by Sprayed Water—

By the way, in the above-described operation, oil mist included in air adheres to the surface of the dust collecting electrode sections (31b) one after another. This causes a risk where the surface of the dust collecting electrode section (30b) (dust collecting face in particular) may be covered with oil for example. The undesirably dirty dust collecting face as described above reduces an effective surface area contributing to the dust capturing, thus undesirably causing a deteriorated performance for collecting dust such as oil mist. To prevent this, according to this embodiment, the sprayed water from the spray nozzle (21) is used to clean the dust collecting electrode section (31b).

Specifically, the sprayed water sprayed through the spray nozzle (21) drips down by its own weight. Then, the water flows down together with air and is actively sent to the surfaces of the first electrode plates (31) and the second electrode plates (32). As a result, oil adhered to the dust collecting electrode sections (31b) for example is washed away by the sprayed water. When oil adheres to the second electrode plates (32) and the ionization electrodes (33), this oil is also washed away by the sprayed water. Furthermore, the first electrode plate (31) and the second electrode plate (32), which are provided perpendicularly, allow the sprayed water to flow down along the surfaces of the respective electrode plates (31, 32). This provides an increased cleaning effect to the respective electrode plates (31, 32).

In addition, since sprayed water includes the above active species, the active species gradually causes the oxidation decomposition of the oil adhered to the surfaces of the respective electrode plates (31, 32). As a result, the oil for example turns into hydrophilic substance and thus can be easily dissolved in sprayed water, thus providing a further-improved cleaning effect to the respective electrodes plates (31, 32).

In the charged dust collecting section (30), an effective dust collecting area is secured by appropriately cleaning the dust collecting faces for example of dust collecting electrode sections (31b). Thus, the charged dust collecting section (30) can retain a desired dust collecting performance for a long period.

As described above, according to the air processing device (10) of this embodiment, the current-carrying section (45), which electrically connects the power source (23) to the electric discharge spray section (20) and electrically connects the power source (34) to the charged dust collecting section (30) respectively, is attached via the insulating member (40) to the casing (11). This insulating member (40) is composed of the covering section (46) and the tube-like section (41). This can consequently secure a sufficient insulating performance among the electric discharge spray section (20), the charged dust collecting section (30), and the casing (11) even when water droplets adhered to the insulating member (40) cause current flowing over the surface of the insulating member (40) via the water droplets.

Specifically, current flowing over the surface of the insulating member (40) via water droplets firstly flows from the electric discharge spray section (20) and the charged dust collecting section (30) via the surface of the covering section (46) and reaches the tube bottom section (41a) of the tube-like section (41). Then, current flows over the tube inner periphery face of the tube-like section (41) and moves to the opening-side and then flows over the tube outer periphery face and reaches the casing (11). This can consequently secure a long insulating distance from the electric discharge spray section (20) and the charged dust collecting section (30) via the current-carrying section (45) to the casing (11). Thus, the electric discharge spray section (20) and the charged dust collecting section (30) and the casing (11) can have an improved insulating performance therebetween.

INDUSTRIAL APPLICABILITY

As described above, the present invention is significantly useful and is highly-applicable in the industry because the invention can provide a highly-practical air processing device by which the respective electrodes and the casing can have an improved insulating performance therebetween even under an environment where water droplets are supplied.

The invention claimed is:

1. An air processing device including an electric discharge processing section that is provided in an air passageway in a casing supplied with water droplets and that applies a voltage to perform electric discharge, comprising:

a current-carrying section that electrically connects a power source exterior to the casing to the electric discharge processing section to apply a voltage to the electric discharge processing section and that is attached to the casing via an insulating member having an insulation property, wherein the insulating member includes:

a covering section covering an outer periphery face of the current-carrying section, and a tube-shaped section that is formed to have a tube shape having a bottom, that is attached to the casing so that an opening-side end is positioned in the air passageway, and that is structured so that a power source-side end of the covering section is supported by a tube bottom section so that the current-carrying section extends through the tube in a tube axis direction.

2. The air processing device according to claim 1, wherein at a predetermined position in the covering section at a tube inner side with respect to an opening-side end of the tube-shaped section, a flange section is provided that suppresses water from moving to the tube inner side along an outer periphery face of the covering section.

3. The air processing device according to claim 1, wherein the tube-shaped section of the insulating member is attached to the casing so that an opening-side end is downwardly inclined.

4. The air processing device according to claim 1, wherein the current-carrying section is horizontally attached to the casing via the insulating member, and a drainage channel that extends in a tube axis direction and that is downwardly inclined to an opening-side end is formed at the lowest part at an inner periphery face of the tube-shaped section.

5. The air processing device according to claim 1, wherein at a predetermined position in an inner periphery face of the tube-shaped section in a tube axis direction, a protrusion section is provided that protrudes in a tube inner diameter direction and that suppresses water from moving along an inner periphery face of the tube-shaped section to a tube inner side.

6. The air processing device according to claim 1, wherein an air hole for introducing air from the outside of the casing into the air passageway is formed at the tube bottom section of the tube-shaped section.

* * * * *